(12) United States Patent
Thomas et al.

(10) Patent No.: US 9,404,836 B2
(45) Date of Patent: Aug. 2, 2016

(54) METHOD AND DEVICE FOR CARBONYL DETECTION AND QUANTITATION

(71) Applicant: Pulse Health LLC, Portland, OR (US)

(72) Inventors: Gerald Thomas, Springfield, OR (US); Brian Young, Portland, OR (US); Juven Lara, Portland, OR (US); Charles Noll, Portland, OR (US); James Ingle, Corvallis, OR (US)

(73) Assignee: Pulse Health LLC, Portland, OR (US)

( * ) Notice: Subject to any disclaimer, the term of this patent is extended or adjusted under 35 U.S.C. 154(b) by 0 days.

(21) Appl. No.: 14/754,567

(22) Filed: Jun. 29, 2015

(65) Prior Publication Data

US 2015/0377858 A1 Dec. 31, 2015

Related U.S. Application Data

(60) Provisional application No. 62/156,441, filed on May 4, 2015, provisional application No. 62/149,988, filed on Apr. 20, 2015, provisional application No. 62/018,448, filed on Jun. 27, 2014.

(51) Int. Cl.
*G01N 33/497* (2006.01)
*G01N 33/48* (2006.01)
*G01N 33/58* (2006.01)
*G01N 1/22* (2006.01)
*G01D 11/24* (2006.01)
*G01N 33/52* (2006.01)
*G01N 21/64* (2006.01)

(52) U.S. Cl.
CPC .................. *G01N 1/22* (2013.01); *G01D 11/24* (2013.01); *G01N 21/6428* (2013.01); *G01N 33/497* (2013.01); *G01N 33/4972* (2013.01); *G01N 33/52* (2013.01); *G01N 21/645* (2013.01); *G01N 2001/2244* (2013.01); *G01N 2021/6482* (2013.01); *G01N 2033/4975* (2013.01); *G01N 2201/022* (2013.01); *G01N 2201/062* (2013.01); *G01N 2201/068* (2013.01); *Y10T 436/200833* (2015.01); *Y10T 436/202499* (2015.01)

(58) Field of Classification Search
CPC .................. Y10T 436/20; Y10T 436/202499; Y10T 436/200833; G01N 33/497; G01N 33/483; G01N 33/48; G01N 33/00
USPC .................................................. 436/128, 127
See application file for complete search history.

(56) References Cited

U.S. PATENT DOCUMENTS

| | | |
|---|---|---|
| 3,094,511 A | 6/1963 | Hill, Jr. et al. |
| 3,446,773 A | 5/1969 | Schwarz |
| 4,080,170 A | 3/1978 | Borkenstein |
| 4,184,850 A | 1/1980 | Habenstein |
| 4,438,206 A | 3/1984 | Nakajima et al. |
| 4,548,904 A | 10/1985 | Kent et al. |
| 4,552,849 A | 11/1985 | Nakajima |
| 5,081,871 A | 1/1992 | Glaser |
| 5,174,959 A | 12/1992 | Kundu et al. |
| 5,254,261 A | 10/1993 | Tomaschke et al. |
| 5,284,054 A | 2/1994 | Loebach |
| 5,310,682 A | 5/1994 | Novotny et al. |
| 5,465,728 A | 11/1995 | Phillips |
| 5,585,469 A | 12/1996 | Kojima et al. |
| 5,739,535 A | 4/1998 | Koch et al. |
| 5,801,059 A | 9/1998 | Smith et al. |
| 5,924,994 A | 7/1999 | Harbrecht et al. |
| 6,019,731 A | 2/2000 | Harbrecht et al. |
| 6,023,982 A | 2/2000 | Basch et al. |
| 6,136,608 A | 10/2000 | Kawachi |
| 6,138,521 A | 10/2000 | Basch et al. |
| 6,242,267 B1 | 6/2001 | Herron et al. |
| 6,315,688 B1 | 11/2001 | McLaughlin et al. |

(Continued)

FOREIGN PATENT DOCUMENTS

| | | |
|---|---|---|
| EP | 2606820 A1 | 6/2013 |
| EP | 2641537 A1 | 9/2013 |
| WO | 94/06057 | 3/1994 |
| WO | 96/38724 | 12/1996 |
| WO | 2009/094536 | 7/2009 |
| WO | 2010/009406 | 1/2010 |
| WO | 2012120140 | 9/2012 |
| WO | 2013115933 | 8/2013 |
| WO | 2013172873 | 11/2013 |
| WO | 2014116604 | 7/2014 |
| WO | 2014/165184 | 10/2014 |

OTHER PUBLICATIONS

Xu, et al. "Fluorescence Ratiometric Sensor for Trace Vapor Detection of Hydrogen Peroxide," Applied Materials and Interfaces, 2014, 6, 8708-8714; May 7, 2014.

(Continued)

*Primary Examiner* — Christine T Mui
(74) *Attorney, Agent, or Firm* — Brownstein Hyatt Farber Schreck, LLP; Cara L. Crowley-Weber (57) ABSTRACT

Fluorescence chromophores such as phenylene diamine derivatives can undergo oxidative coupling and polymerization to form optical, colorimetric and fluorogenic, multimers and polymers. The presence of carbonyl containing moieties such as aldehydes and ketones under favorable environmental conditions can initiate, catalyze, accelerate and modulate this reaction which in turn provides a mechanism for the detection and quantitation of such moieties. Selected phenylene diamine derivatives can be used for the detection and quantitation of aldehyde and ketones via measurement of the reaction and the associated spectroscopic transformation. In particular, the use of meta-phenylene diamine (mPDA) and related compounds for aldehyde detection and quantitation is described. The method provides a convenient means for monitoring aldehyde and ketone levels without use of separation steps. The method is applicable to kinetic and quasi-endpoint detection assay formats.

31 Claims, 8 Drawing Sheets

(56) References Cited

U.S. PATENT DOCUMENTS

| | | |
|---|---|---|
| 6,462,128 B1 | 10/2002 | Barashkov et al. |
| 6,582,376 B2 | 6/2003 | Baghdassarian |
| 6,632,402 B2 | 10/2003 | Blazewicz et al. |
| 6,835,431 B1 | 12/2004 | Alperovich et al. |
| 7,032,431 B2 | 4/2006 | Baum et al. |
| 7,087,434 B2 | 8/2006 | Chen et al. |
| 7,101,716 B2 | 9/2006 | Nakano et al. |
| 7,153,272 B2 | 12/2006 | Talton |
| 7,220,387 B2 | 5/2007 | Flaherty et al. |
| 7,312,071 B2 | 12/2007 | Lu et al. |
| 7,347,825 B2 | 3/2008 | Vaughan et al. |
| 7,352,465 B2 | 4/2008 | Fay et al. |
| 7,384,793 B2 | 6/2008 | McCash et al. |
| 7,432,298 B2 | 10/2008 | Lam et al. |
| 7,514,265 B2 | 4/2009 | Yoon et al. |
| 7,533,558 B2 | 5/2009 | Flaherty et al. |
| 7,547,285 B2 | 6/2009 | Kline |
| 7,560,574 B2 | 7/2009 | Habi et al. |
| 7,790,467 B1 | 9/2010 | Massick |
| 7,833,480 B2 | 11/2010 | Blazewicz et al. |
| 7,992,422 B2 | 8/2011 | Leddy et al. |
| 8,002,712 B2 | 8/2011 | Meka et al. |
| 8,012,761 B2 | 9/2011 | Boga et al. |
| 8,026,103 B2 | 9/2011 | Van Herpen et al. |
| 8,181,503 B2 | 5/2012 | Flaherty et al. |
| 8,198,097 B1 | 6/2012 | Pera |
| 8,383,672 B2 | 2/2013 | Habi et al. |
| 8,394,030 B2 | 3/2013 | Varga et al. |
| 8,618,161 B2 | 12/2013 | Lam et al. |
| 8,628,975 B2 | 1/2014 | Lam et al. |
| 8,642,966 B2 | 2/2014 | Weckstrom et al. |
| 8,772,487 B2 | 7/2014 | Chen et al. |
| 8,778,693 B2 | 7/2014 | Boudenne et al. |
| 8,809,531 B2 | 8/2014 | Bremberg et al. |
| 8,821,409 B2 | 9/2014 | Ku et al. |
| 8,950,240 B2 | 2/2015 | Yeh et al. |
| 2003/0208133 A1 | 11/2003 | Mault |
| 2004/0017570 A1 | 1/2004 | Parikh et al. |
| 2004/0162500 A1 | 8/2004 | Kline |
| 2005/0084921 A1 | 4/2005 | Cranley et al. |
| 2006/0073604 A1 | 4/2006 | Yoon et al. |
| 2006/0266353 A1 | 11/2006 | Yamada et al. |
| 2007/0062255 A1 | 3/2007 | Talton |
| 2007/0093725 A1 | 4/2007 | Shaw |
| 2008/0204705 A1 | 8/2008 | Liu |
| 2008/0234553 A1 | 9/2008 | Urman et al. |
| 2009/0159803 A1 | 6/2009 | Berthold et al. |
| 2009/0162891 A1 | 6/2009 | Lu et al. |
| 2010/0178662 A1 | 7/2010 | Urman et al. |
| 2010/0256514 A1 | 10/2010 | Chazan et al. |
| 2011/0003395 A1 | 1/2011 | Dey et al. |
| 2011/0098590 A1* | 4/2011 | Garbutt ............... A61B 5/0059 600/532 |
| 2012/0004571 A1 | 1/2012 | Ku et al. |
| 2012/0011918 A1 | 1/2012 | Bacal et al. |
| 2012/0071342 A1 | 3/2012 | Lochhead et al. |
| 2012/0105949 A1 | 5/2012 | Cummings et al. |
| 2012/0165694 A1 | 6/2012 | Meka et al. |
| 2012/0276651 A1 | 11/2012 | Kim et al. |
| 2012/0302907 A1 | 11/2012 | Palmskog et al. |
| 2013/0006068 A1 | 1/2013 | Gemer et al. |
| 2013/0253336 A1 | 9/2013 | Haveri et al. |
| 2013/0276509 A1 | 10/2013 | Rathke et al. |
| 2013/0281873 A1 | 10/2013 | Evans et al. |
| 2013/0288911 A1 | 10/2013 | Chen et al. |
| 2013/0305808 A1 | 11/2013 | Yoo |
| 2014/0171635 A1 | 6/2014 | Schwartz et al. |
| 2014/0202234 A1 | 7/2014 | Burgon et al. |
| 2014/0220696 A1 | 8/2014 | Schwartz et al. |
| 2014/0373649 A1 | 12/2014 | Harrell et al. |
| 2015/0073290 A1 | 3/2015 | Star et al. |

OTHER PUBLICATIONS

International Search Report & Written Opinion dated Sep. 30, 2015; PCT/US2015/038389.

International Search Report & Written Opinion dated Sep. 30, 2015; PCT/US2015/038391.

International Search Report & Written Opinion dated Sep. 29, 2015; PCT/US2015/038392.

Mallya et al., "Organic Molecule Based Sensor for Aldehyde Detection," Abstract, Sensing Technology: Current Status and Trends III, Smart Sensors, Measurement and Instrumentation vol. 11, 2015, pp. 299-325. http://link.springer.com/chapter/10.1007%2F978-3-319-10948-0_15.

Fink, Johannes, Petroleum Engineer's Guide to Oil Field Chemicals and Fluids, First Edition, Gulf Professional Publishing, p. 188, May 2011.

Marinho et al., "The reaction of α-phenylenediamine with ethoxymethylene compounds and aromatic aldehydes," ARKIVOC 2009 (xiv) pp. 346-361.

Dunn, Connie Dee, Automated Determination of Carbonyl Compounds in Organic Solvents, a Thesis in Chemistry, Aug. 1992.

Stejskal, Jaroslav, "Polymers of phylendiamines," Progress in Polymer Science, 41(2015) pp. 1-31.

International Search Report and Written Opinion dated Sep. 25, 2015; PCT/US2015/038394.

* cited by examiner

| Aldehyde (C#) | Relative Response to Hexanal (Counts-30 min) |
|---|---|
| C2 | 0.1275 |
| C3 | 0.1248 |
| C6 | 1.0000 |
| C10 | 1.3041 |

METHOD AND DEVICE FOR CARBONYL DETECTION AND QUANTITATION

CROSS REFERENCE TO RELATED APPLICATIONS

This application claims the benefit of U.S. Provisional Application No. 62/156,441, filed May 4, 2015, U.S. Provisional Application No. 62/149,988, filed Apr. 20, 2015, and U.S. Provisional Application No. 62/018,448, filed Jun. 27, 2014, which are all incorporated by reference herein in their entireties.

FIELD OF THE INVENTION

The present invention is directed to the field of carbonyl detection and quantitation, and in particular the detection and quantitation of the concentration of carbonyl containing moieties in biological samples.

BACKGROUND OF THE INVENTION

The detection of carbonyl containing moieties is known but the precise detection of specific low concentrations of specific carbonyl containing moieties in biological samples is not known. The use of carbonyl's to induce the polymerization of o-phenylene diamine and p-phenylene diamine at high temperature is known to produce solid polymers for subsequent use in manufacturing products, but the use of phenylene diamine derivatives is not known to be used in methods to detect carbonyl containing moieties in a number of biological samples. In addition, measuring the fluorescence of a fluorogenic species in a solution to determine the presence of molecules corresponding to the species is known, as well as the quantitation of the concentration of such molecules in a given sample. Further analyzing carbonyls in biological samples is known, see, e.g., Publication No. US 2003/0208133 published Nov. 6, 2003 and Publication No. US 2011/0003395 published Jan. 6, 2011, both of which are incorporated herein in their entirety.

SUMMARY OF THE PREFERRED EMBODIMENTS

One embodiment of the present invention is directed to a method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution.

Another embodiment of the present invention is directed to a solution containing an alcohol, a salt, a surfactant, a phenylene diamine derivative and a carbonyl containing moiety.

Yet another embodiment of the present invention is directed to a substantially precipitate free solution containing the product of a meta-phenylene diamine derivative and a carbonyl containing moiety.

Another embodiment of the present invention is directed to a method of detecting and measuring the concentration of a carbonyl containing moiety in a biological sample, the method comprising
a) isolating the carbonyl containing moiety from the biological sample;
b) adding the carbonyl containing moiety to an aqueous solution containing a phenylene diamine derivative to form a fluorescing solution; and
c) measuring the fluorescence emitted from the fluorescing solution at a pre-determined wave length.

Another embodiment of the present invention is directed to a method of detecting and measuring the concentration of aldehydes in a human breath sample, the method comprising:
a. capturing the aldehydes from the human breath sample on silica;
b. forming a solution comprising a salt, a buffer, a surfactant in an alcohol in mildly acidic conditions;
c. adding a phenylene diamine derivative to the solution of step b;
d. eluting the captured aldehydes into the solution of step c;
e. determining the fluorescence signal of the solution of step c;
f. determining the fluorescence signal of the solution of step d;
g. subtracting the fluorescence signal from step e from the fluorescence signal from step f; and
h. comparing the net resulting fluorescence signal from step g with standard fluorescence of known aldehydes to determine the concentration of aldehydes in the fluorescing solution.

Another embodiment of the present invention is directed to a device comprising:
a) a breath chamber having a substrate, the substrate supporting a carbonyl containing moiety from an animal's breath; and
b) a fluid chamber having an aqueous solution comprising an alcohol, a salt, a surfactant, and a buffer.

Yet another embodiment of the present invention is directed to a device for detecting and quantitating the concentration of a carbonyl containing moiety in a biological sample, the device comprising a substrate having an active reactive capture agent incorporated therein.

Another embodiment of the present invention is directed to a method for detecting carbonyl containing moieties in a biological sample, the method comprising the steps of providing a substrate having an active reactive capture agent incorporated therein, capturing on said substrate carbonyl containing moieties from the biological sample, and forming a solution comprising painted carbonyl containing moieties.

Yet another embodiment of the present invention is directed to a method for detecting carbonyl containing moieties in a biological sample, the method comprising the steps of:

a. providing a substrate;
b. incorporating an active reactive capture agent into the substrate;
c. capturing carbonyl containing moieties on the substrate; and
d. eluting the active reactive capture agent and carbonyl containing moieties from the substrate into a solution whereby painted carbonyl containing moieties are formed.

Another embodiment of the present invention is directed to a method of detecting carbonyl containing moieties in a biological sample, the method comprising adding a fluorescence chromophore to an aqueous salt solution to thereby form a fluorescence chromophore solution; adding a carbonyl containing moiety from the biological sample to the fluorescence chromophore solution to thereby form a fluorescing solution; and detecting fluorescence from the fluorescing solution.

DETAILED DESCRIPTION OF THE PREFERRED EMBODIMENTS

The following description and figures are illustrative and are not to be construed as limiting. Numerous specific details are described to provide a thorough understanding of the disclosure. However, in certain instances, well-known or conventional details are not described in order to avoid obscuring the description. Reference in this specification to "one embodiment" or "an embodiment" means that a particular feature, structure, or characteristic described in connection with the embodiment is included in at least one embodiment of the disclosure. References to one or another embodiment in the present disclosure can be, but not necessarily are, references to the same embodiment; and, such references mean at least one of the embodiments, nor are separate or alternative embodiments mutually exclusive of other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term.

The present invention is directed to a method and device useful for the detection, quantitation and assay of carbonyl containing moieties ("CCM") including aldehydes, preferably in biological samples, and preferably at low concentrations in the biological sample. In this regard, CCM is defined to include one or more different carbonyl containing moieties.

As used herein, a "biological sample" is referred to in its broadest sense, and includes solid and liquid or any biological sample obtained from nature, including an individual, body fluid, cell line, tissue culture, or any other source. As indicated, biological samples include body fluids or gases, such as breath, blood, semen, lymph, sera, plasma, urine, synovial fluid, spinal fluid, sputum, pus, sweat, as well as liquid samples from the environment such as plant extracts, pond water and so on. Solid samples may include animal or plant body parts, including but not limited to hair, fingernail, leaves and so on. The preferred biological sample for one embodiment of the present invention is the breath of a human.

A CCM is a compound having at least one carbonyl group. A carbonyl group is the divalent group >C=O, which occurs in a wide range of chemical compounds. The group consists of a carbon atom double bonded to an oxygen atom. The carbonyl functionality is seen most frequently in three major classes of organic compounds: aldehydes, ketones, and carboxylic acids. As used herein, "aldehyde" has its ordinary chemical meaning and the method of the present invention is useful in detecting the concentration of aldehydes in biological samples. In particular, the present invention is useful in detecting various forms of aldehydes include without limitation 1-hexanal, malondialdehyde, 4-hydroxynonenal, acetaldehyde, 1-propanal, 2-methylpropanal, 2,2-dimethylpropanal, 1-butanal, and 1-pentanal.

The amount of the CCM captured by the substrate may vary, but typically for a substrate consisting of 200 mg of 50-270 mesh (300-50 µm) particle with a bed diameter of 12.5 mm, generally, it will be equivalent to the amount in a human's breath after breathing into a tube like a breathalyzer. Preferably it will be from 75 to 0.1 ppb (400 to 4 pmoles) and more preferably from 20 ppb to 0.01 ppb (80 to 0.4 pmoles).

The invention is amenable to "mix & read" and "real-time" assay formats for the detection of CCM. The invention can be applied to the detection of CCM in solution. The invention can be applied to the detection of trace CCM in the gas phase by the addition of a primary capture (on a substrate as discussed below) and release (elution from the loaded substrate as discussed below) process. Preferably in one step of the process, gas phase CCM, for example, aldehydes from the breath of a human, are captured on a substrate.

The substrate of the present invention is desirably formed from a solid, but not necessarily rigid, material. The solid substrate may be formed from any of a variety material, such as a film, paper, nonwoven web, knitted fabric, woven fabric, foam, glass, etc. For example, the materials used to form the solid substrate may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous matrix, with polymers such as vinyl chloride, vinyl chloridepropylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. Preferably the substrate is a solid phase matrix of silica optionally spaced between frits. The size of the substrate is chosen so that a measurable amount of CCM is captured by the substrate. The size can vary but generally it is about 2 mL, preferably about 1 mL and more preferably about 0.25 mL.

The substrate typically consists of a bed of particles with 50-60 angstrom pores, with a 50-270 mesh (300-50 μm), and a mass of 75 to 300 mg, preferably 60-120 mesh (250-125 μm) with a mass of 100 to 200 mg and more preferably 50-120 mesh (210-125 μm) with a mass of 125 to 175 mg.

Figure 1A:
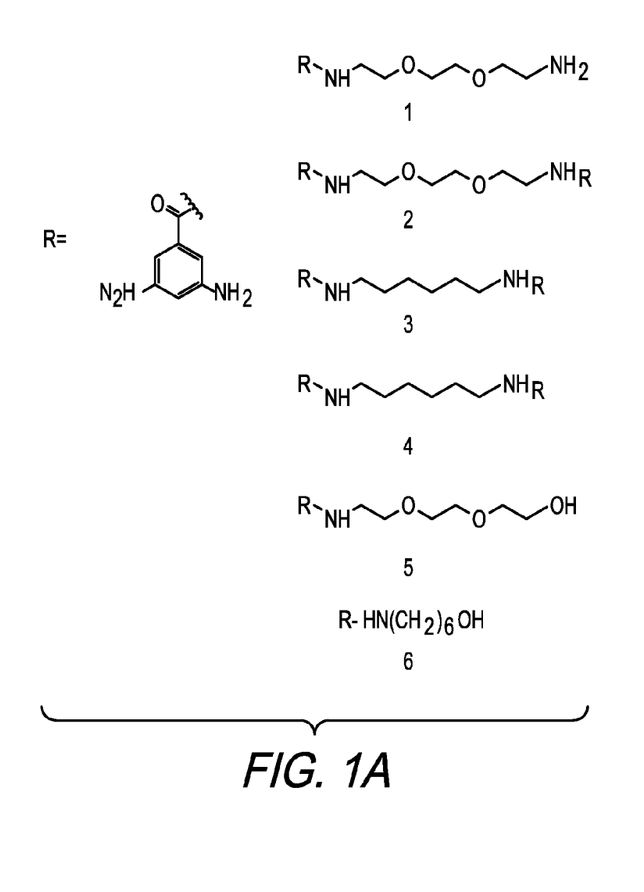
FIG. 1A shows alternative phenylene diamine derivatives with reduced surfactant dependency.

In another step of the process, a fluorescence chromophore such as a phenylene diamine derivative is added to an elution solution to form a phenylene diamine solution. Phenylene diamine derivatives useful in connection with the present invention include but are not limited to many phenylene diamine derivatives including without limitation meta-phenylene diamine ("mPDA") and its derivatives, and those shown in FIG. 1A and FIG. 1B, with mPDA preferred for detecting aldehydes including without limitation 1-hexanal. While certain p-PDA or o-PDA derivatives may be useful in the method of the present invention, they are not useful for detecting 1-hexanal as they yield a cloudy colloidal suspension which is not useful for the optical based detection discussed below.

Other phenylene diamine derivatives include the following or mixtures thereof:

Where R1, R2, R3, R4 are each independently selected from the group consisting of H, alkyl, substituted alkyl, alkoxy, substituted alkoxy, acyl, acylamino, acyloxy, amino, substituted amino, aminocarbonyl, aminothiocarbonyl, aminocarbonylamine, aminothiocarbonylamino, aminocarbonyloxy, aminosulfonyl, aminosulfonyloxy, aminosulfonylamino, amidino, carboxyl, carboxyl ester, (carboxylester) amino, (carboxyl ester) oxy, cyano, halo, hydroxy, SO3-, sulfonyl, substituted sulfonyl, sulfonyloxy, thioacyl, thiol, alkylthio, substituted alkylthio, acyl, substituted aryl, heteroaryl, substituted heteroaryl, cycloalkyl, substituted cycloalkyl, heterocycles, and substituted heterocycles.

Figure 1B:
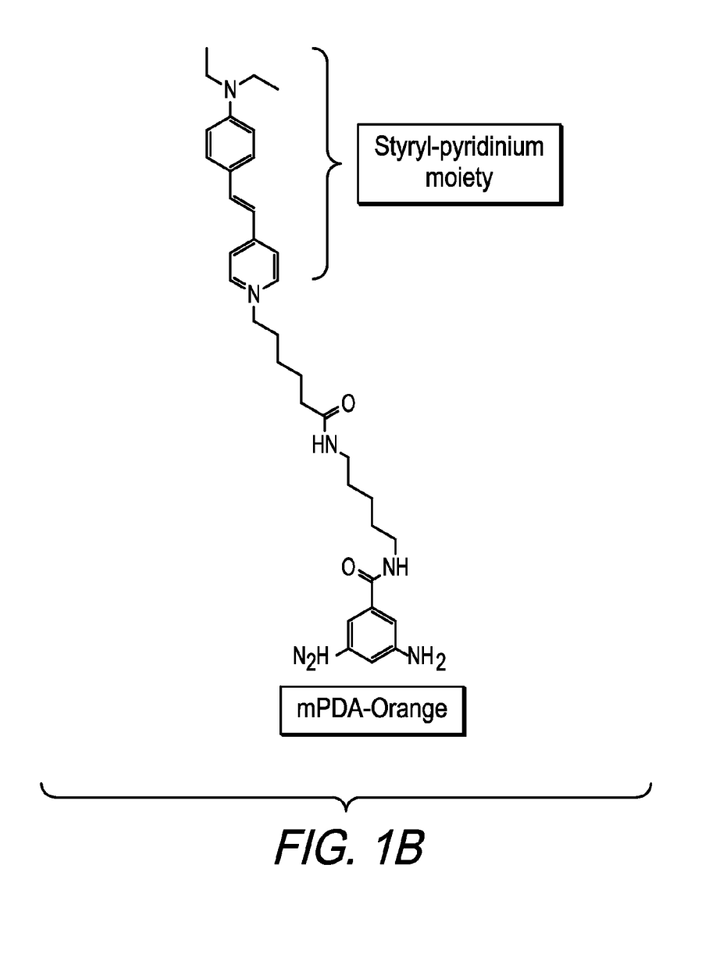
FIG. 1B shows an alternative phenylene diamine derivative.
Figure 1C:
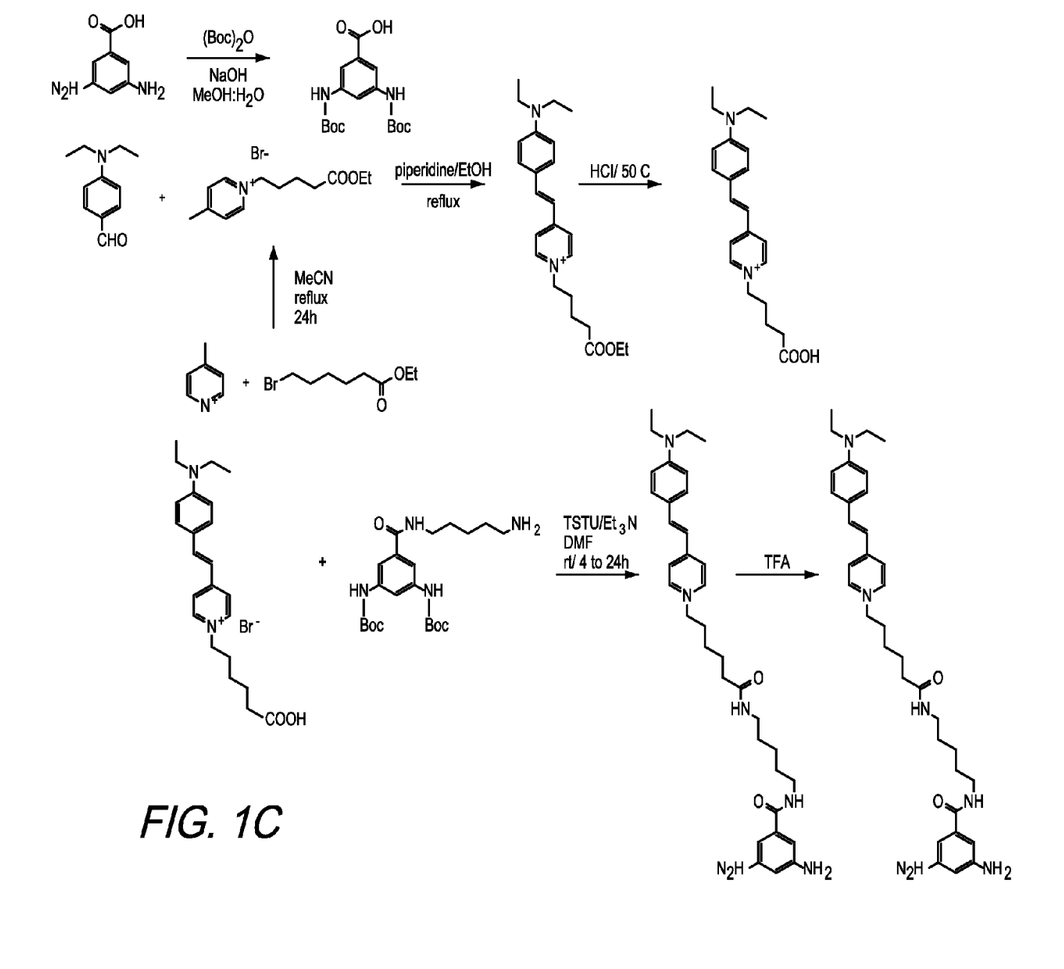
FIG. 1C shows a pathway for the synthesis of the alternative phenylene diamine derivative shown in FIG. 1B.
Figure 1D:
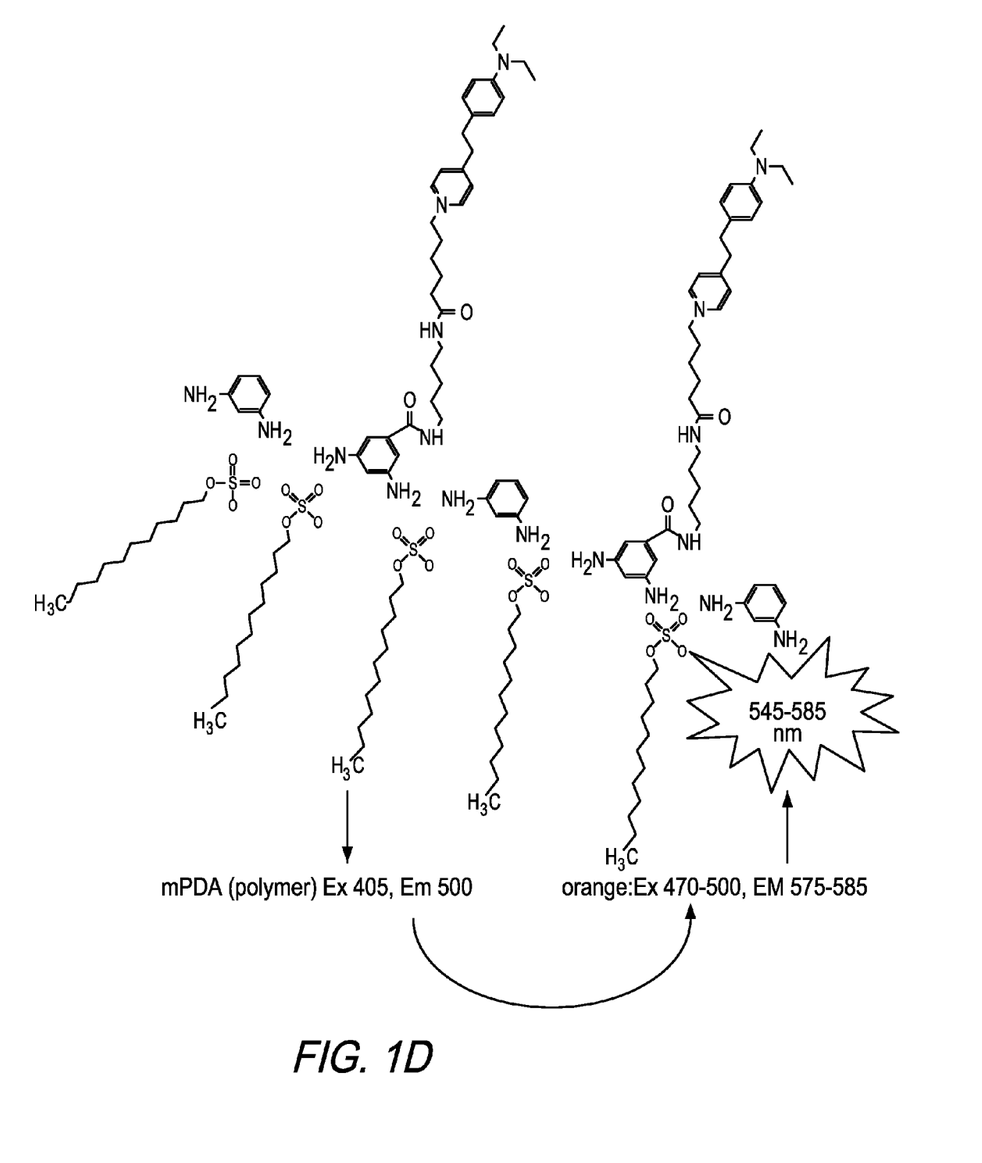
FIG. 1D shows an illustration of a FRET response of the alternative phenylene diamine derivative shown in FIG. 1B to aldehyde induced polymerization of m-phenylene diamine.

With reference to FIG. 1B, mPDA-Orange, namely, pyridinium,4-[2-[4-(diethylamino)phenyl-ethenyl]-1-[1-(3,5-diminobenzamide)-pentylamino-5-oxyhexyl], is shown. The mPDA derivative mPDA-orange leverages both a) the sensitivity to environmental changes and b) the potential to modulate the surfactant dependence of the mPDA-aldehyde induced polymerization. The scheme used to synthetize mPDA-orange is illustrated in FIG. 1C. The basic scheme was to conjugate mPDA to the styrylpyridinium moiety via an alkyl amide linker.

mPDA-orange exhibits a quantum yield increase as the molecule is incorporated into the aldehyde induced mPDA polymer. In addition, the excitation and emission properties of the styrylpyridinium moiety affords a FRET (Forster Energy Transfer) generated signal from the mPDA polymer. The styrylpyridinium moiety exhibits a broad excitation with a maximum at 470 nm and an emission maximum at 570 nm. The excitation profile provides sufficient overlap with the emission profile of the mPDA polymer to afford FRET based signal generation. A FRET based signal generation would be manifest by an excitation at the mPDA polymer (405 nm) and emission at the styrylpyridinium moiety emission at 570 nm. An illustration of a FRET response of mPDA-orange to aldehyde induced polymerization of mPDA is displayed in FIG. 1D.

Figure 1E:
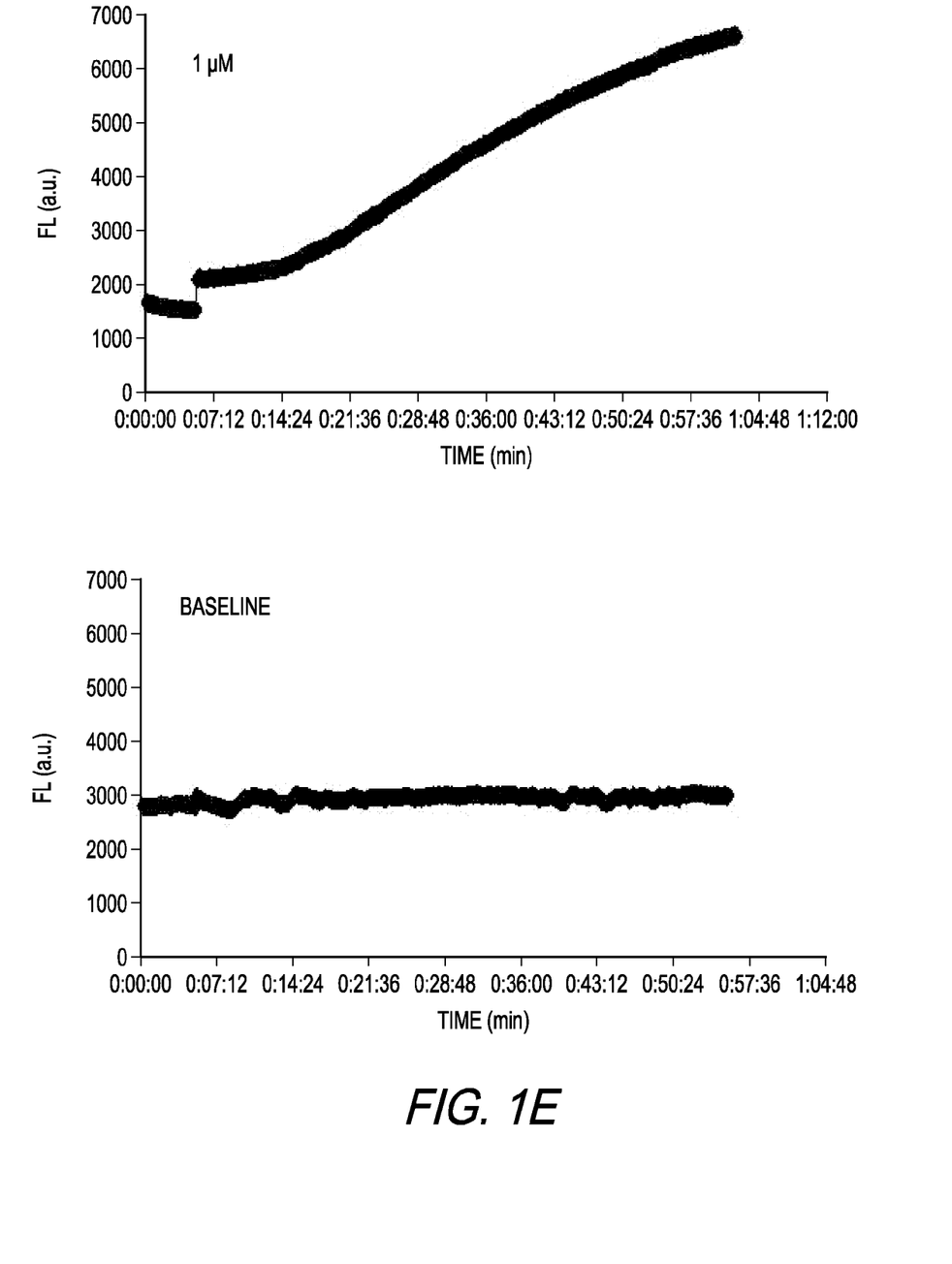
FIG. 1E shows graphs plotting the increase in fluorescence of the alternative phenylene diamine derivative shown in FIG. 1B in the presence of 1 µM hexanal.

A direct aldehyde induced polymerization of mPDA-orange alone does not generate a response signal due to quenching of the styrylpyridinium at the high concentrations required for induction of the polymer. A response would only be expected when the mPDA-orange is contained within a mixture of mPDA and mPDA-orange. Indeed, an aldehyde response is only observed when mPDA-orange is doped into mPDA at significantly dilute molar ratios mPDA/mPDA-orange 1,000:1 to 10,000:1. The response to aldehyde is illustrated in FIG. 1E. An increase in mPDA-Orange emission at 570 nm is observed when excited at 405 nm when 1 μM hexanal is added to the system. The increase in emission is not observed when the mPDA-orange styrylpyridinium moiety is excited directly at 470-490 nm. The response is approximately 3× over the background, see FIG. 1E, where the conditions are 7 mM mPDA, 5 μM mPDA-orange (molar ratio 15,000:1), 90 mM NaCl, 15% Ethanol, 0.1% SDS, 50 mM citrate at ph 2.5. The excitation is at 405 nm and the emission at 575-585 nm. As can be seen, in the absence of aldehyde the background level remains fairly constant and auto induction leading to incorporation of mPDA-orange appears to be minimal Though the response for mPDA-orange is much less 3× versus 15× for mPDA alone the derivative offers several advantages: 1) increase wavelength discrimination afforded by the largeStokes shift between excitation and emission and 2) the enhanced baseline stability In general, the concentration of the phenylene diamine derivative in the phenylene diamine solution ranges from 0.5 mM to 25 mM. For mPDA, the mPDA concentration in the phenylene diamine solution generally ranges from 0.5 to 21 mM, preferably from 2 to 10 mM, and optimally 5 mM for aldehydes such as 1-hexanal. Notwithstanding the foregoing, for mPDA-orange, it must be diluted into mPDA at a low molar ratio, preferably 1000-10,000.

In general, the elution solution includes a salt, a buffer, a surfactant, and an organic solvent. The concentration of the salt ranges can from 5 mM to 200 mM and preferably from 20 mM to 80 mM; the concentration of the buffer can range from 25 mM to 200 mM and preferably from 40 mM to 60 mM; and the concentration of the surfactant can range from 0.05% (1.7 mM) to 0.4% (13.9 mM), and preferably from 0.15% (5.2 mM) to _0.25% (8.7 mM). Optimally 0.2% or 6.96 mM is used. The salt can be any salt that does not negatively impact the fluorescing solution and controls salting effects in the elution solution, and may include NaCl, LiCl, KCl, sulfates and phosphates, and mixtures thereof, with NaCl preferred.

The buffer is employed to maintain the elution solution mildly acidic and preferably at a pH of between 2 and 4.5, more preferably 2.5. The buffer can be a borate buffer, a phosphate buffer, a citrate buffer, an organic buffer such as HEPES (1-piperazineethane sulphonic acid) or also a TRIS (tris(hydroxymethyl)aminoethane) buffer, preferably a citrate buffer for use in detecting aldehydes.

The surfactant can include sodium decyl sulfate, sodium dodecyl sulfate ("SDS"), sodium tetradecyl sulfate and Standapol ES-1, with SDS including the C10, C12 and C14 version of SDS is preferable. Trition X-100, Ninate 11, Georpon 71, Tetraonic 1357, Cremapor-el, Chemal la-9, Silwet L7900, Surfynly468, Surfactant 10G, and Tween 80 might also be used but they did not provide good results with the preferred elution solution, the CCM 1-hexanal and mPDA.

In the absence of SDS the polymerization and aldehyde response as discussed below is severely inhibited. mPDA is highly water soluble and the presence of SDS may provide a scaffold for organizing and orientating mPDA into a matrix to facilitate the polymerization reaction.

The solvent can include an aqueous solution of EtOH, MeOH, propanol, and isopropanol, with 15% EtOH preferred.

The molar ratio of salt concentration to phenylene diamine concentration is important. Generally the ratio should range from 0.03 to 0.5. For the CCM 1-hexanal, a molar ratio of mPDA to NaCl of 0.165 was found to provide optimal response.

The temperature for practicing the method of the present invention preferably ranges from 15 to 35° C., with 25 to 30° C. more preferred.

For the aldehydes such as 1-hexanal, one preferred embodiment of the elution solution comprises 33 mM NaCl, 50 mM Citrate, pH 2.5, 15% EtOH, and 0.2% SDS. Other preferred elution solutions include 50 mM Citrate, pH2.5, 15% propanol and 0.4% sodium decyl sulfate.

Using the elution solution containing a phenylene diamine derivative, the CCM is eluted into the phenylene diamine solution to form a fluorescing solution. The CCM and the mPDA react to form a fluorogenic species, the presence of which in the fluorescing solution is detected by measuring the fluorescence emitted by the fluorogenic species in the fluorescing solution.

The aldehyde content is quantitated by monitoring the signal rise (end-point) and/or rate of signal change (kinetic) which varies as a function of aldehyde concentration for a given mPDA concentration, and comparing such data with a carbonyl population sample of the breath. In practice the impact of carbonyls other than the selected carbonyl must be filtered out. There are two general assay format or detection modes. They are generally described as end-point and kinetic. In an end-point assay the system is incubated for a set time and the signal read. The signal at that point reflects the amount of analyte in the system. For a positive assay, the greater the concentration of the analyte, the greater the signal increase. In a kinetic assay the rate of change is monitored for a set duration. The rate of change is correlated to the amount of analyte. Preferably the end-point assay is employed with the present invention.

Assay measurements can be made on a typical fluorescence spectrometer including conventional scanning spectrometer, plate-reader or LED/diode based spectrometer following standard assay practices. To illustrate, the data displayed in FIG. 2 was acquired by mixing a total of 2 mL of the reaction solution and aldehyde into a standard fluorescence cuvette and measuring the intensity increase using an LED/diode spectrometer at particular time slices to simulate an end-point determination. The LED/diode spectrometer utilized consisted of an Ocean Optics Jazz spectrometer with LED source and diode detection coupled via fiber optics to a QPOD®-E (Quantum Northwest), which is a temperature controlled fluorescence sample holder. The 405 nm excitation was produced with a violet LED (volts: 3.3 V, I: 0.03 A). The signal was detected using a ILX-5118 diode detection with emission set at 495-505 nm band pass and 250 msec integration. Like most fluorescence based assays, optimal settings are dependent upon the throughput and stray light rejection characteristics of the spectrometer used and must be empirically determined for each instrument.

In one preferred embodiment, the phenylene diamine derivative reacts with the CCM in solution to produce a fluorescence emitting or fluorogenic species. It is believed that the phenylene diamine derivative oxidatively couples to the CCM and the phenylene diamine derivative polymerizes to dimers, trimers, oligomers and/or polymers. It is not clear if the CCM actually becomes part of the growing polymer, although the polymerization is modulated by the presence of CCM and there is a dose response.

The process of using a CCM to polymerize the phenylene diamine derivative may be described as dispersion polymerization. Poly-phenylene diamines have been used to construct nanostructures and colloidal dispersions of different shapes, tubes, spheres and the like. However, if the polymerization results in large high molecular weight structures then precipitation occurs in the solution, which, in the present invention, may handicap optical detection. Thus the ingredients used in the method of the present invention must be chosen to avoid having elements in the fluorescing solution that inhibit detection and quantitation of the CCM.

The present invention utilizes the ability of CCM to modulate (initiate, catalyze and accelerate) the oxidative coupling and polymerization of phenylene diamine derivatives to detect and quantitate trace aldehydes, ketones and carbonyl containing analytes in a biological sample. Oxidative coupling and polymerization of phenylene diamine generates chromophoric and fluorogenic species. In the case of mPDA and aldehydes, the formation of polymers or multimers gives rise to a broad optical absorbance band at 405 nm and an associated emission band at 505 nm. The monomer absorbance is found in the UV region <350 nm. As a result the production of the polymer can be conveniently followed by either conventional absorbance or fluorescence spectroscopy. In this regard, it should be appreciated that the absorbance and emission bands may vary depending upon the CCM and phenylene diamine derivative chosen, but all such bands useful in practicing this invention are part of the invention.

Figure 2:
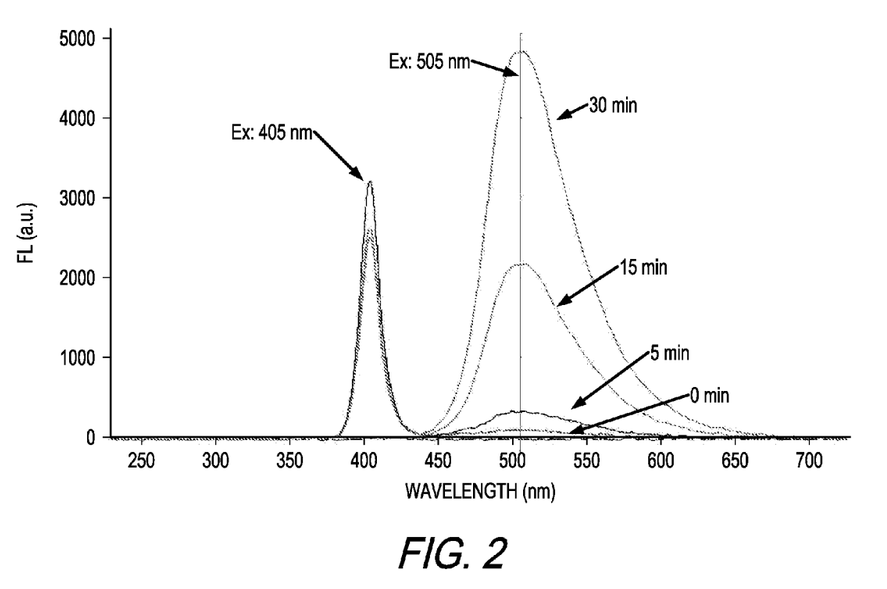
FIG. 2 shows graphs depicting the emission spectrum of the reaction of mPDA with 1-hexanal as a function of time.

For example, with reference to FIG. 2, the emission spectrum of the reaction of mPDA in the presence of 1 μM 1-hexanal as a function of time is shown. The conditions of the fluorescing solution are: 1 μM 1-hexanal, 5.4 mM mPDA, 33 mM NaCl, 50 mM citrate (pH 2.5), 15% EtOH, and 0.1% SDS. The emission increases dramatically as a function of time.

Figure 3:
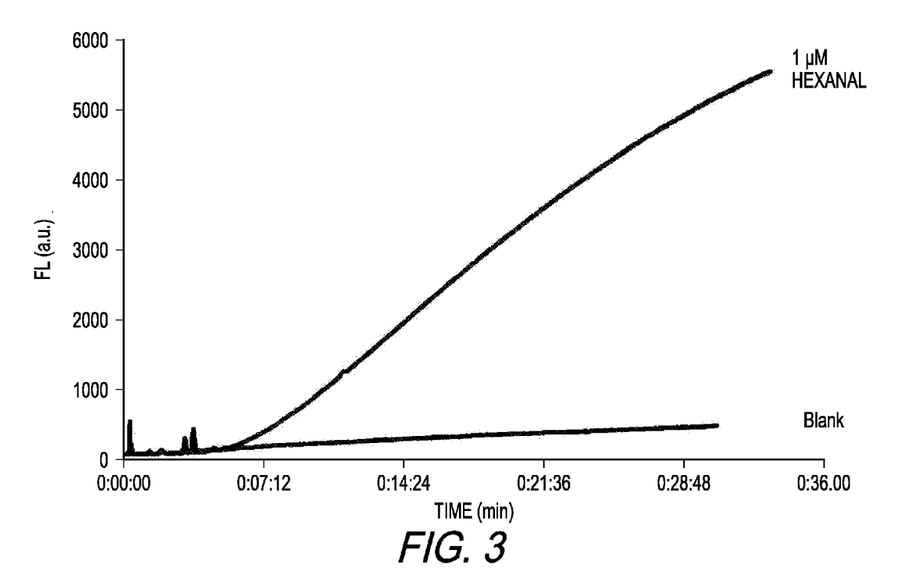
FIG. 3 shows a graph depicting the increase in fluorescence over time of the reaction of mPDA with 1-hexanal being the carbonyl containing moiety.

With reference to FIG. 3, the reaction and responses with and without aldehyde ("blank") are observed. The conditions of the fluorescing solution are: 1 μM 1-hexanal, 5.4 mM mPDA, 33 mM NaCl, 50 mM citrate (pH 2.5), 15% EtOH, and 0.1% SDS. The extent of the emission increase and the rate of increase are dependent upon the concentration of aldehyde in the phenylene diamine solution. At greater aldehyde concentrations, a larger and more rapid signal increase is observed. In the absence of aldehyde, the "blank" under goes a slow gradual small signal rise indicative of the slow polymerization of mPDA under the conditions examined. The polymerization is presumably due to the presence of trace oxidants such as iron, reactive oxygen species and other initiators. With the addition of a CCM, a significant signal enhancement over the blank or background is observed. Of particular note is that the rate of change is easily followed. As a result the detection system is amenable to both kinetic and end-point assay designs and detection modalities. The response can be quantitated at specific time points, e.g., 15 minutes (time slice) or by monitoring the slope as a function of aldehyde. The kinetic rate is slow enough that rapid and high precision of reactant additions is not required. The modulation of the polymerization reaction by a CCM such as an aldehyde and its use as a CCM quantitative sensor is another novel discovery and application described in this specification. Other alternatives including labeling, painting or tagging the CCM for subsequent analysis.

Figure 4A:
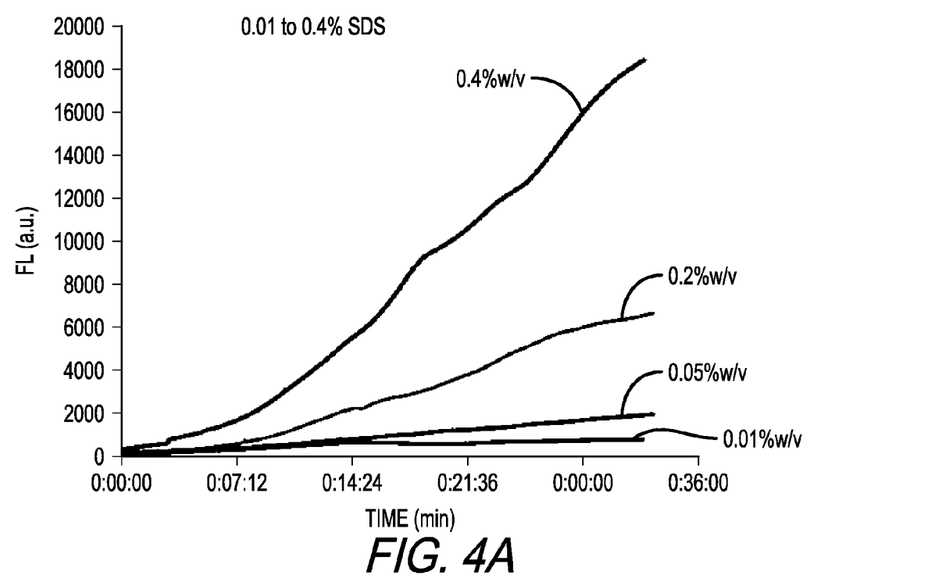
FIG. 4A shows a graph depicting the increase in fluorescence over time of the reaction with 1-hexanal as a function of sodium dodecyl sulfate ("SDS") concentration from 0.01 to 0.4% (w/v).
Figure 4B:
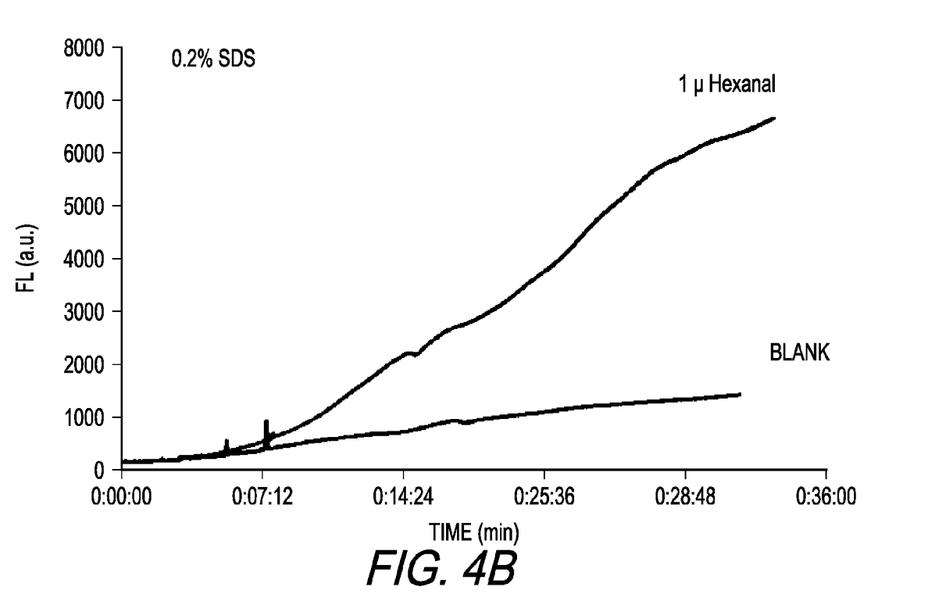
FIG. 4B shows a graph depicting the increase in fluorescence over time of reaction with 1-hexanal as compared to a blank, with SDS concentration at 0.2% SDS.
Figure 4C:
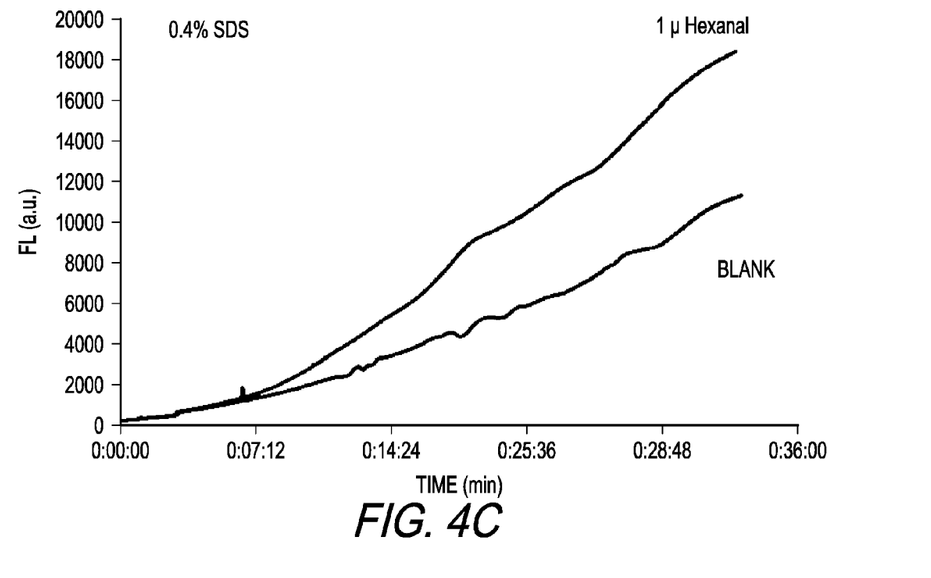
FIG. 4C shows a graph depicting the increase in fluorescence over time of the reaction with 1-hexanal as compared to a blank, with SDS concentration at 0.4% SDS.

With reference to FIGS. 4A, 4B and 4C, the CCM induced polymerization reaction with the phenylene diamine derivative is shown to be sensitive to environmental conditions, and components of the reaction system such as the concentration of SDS. The conditions of the fluorescing solution in these figures are: 1 µM 1-hexanal, 5.4 mM mPDA, 33 mM NaCl, 50 mM citrate (pH 2.5), and 15% EtOH. For example, the reaction and aldehyde assay performance is dependent upon salt content, mPDA content, surfactant, pH and temperature. Since the reaction involves a "quasi-phase" transition from monomer to polymer insufficient mPDA concentration yields a slow reaction with limited signal change. In contrast, a large excess of mPDA results in a very rapid reaction and the formation of insoluble precipitates that limit optical detection. In addition, a large excess results in increased background or "blank" signal.

With reference to FIG. 4A, the signal increases as function of SDS concentration. At an SDS concentration of 0.4%, the signal increase is almost 3 times the signal observed at 0.2%.

FIGS. 4B and 4C show a comparison of the aldehyde response versus the blank for 0.2% SDS and 0.4% SDS, respectively. The increase in SDS concentration also results in an increase in "blank" or background signal. Both the signal and background are modulated by SDS concentration and the optimized SDS concentration cannot be determined by monitoring the signal response alone. As a result the SDS concentration must be optimized to provide the greatest discrimination between signal and background signal generation. For the embodiment specified, the optimal SDS concentration falls within a narrow concentration band, and small deviations can result in increased variability and limit the assay sensitivity.

Figure 5:
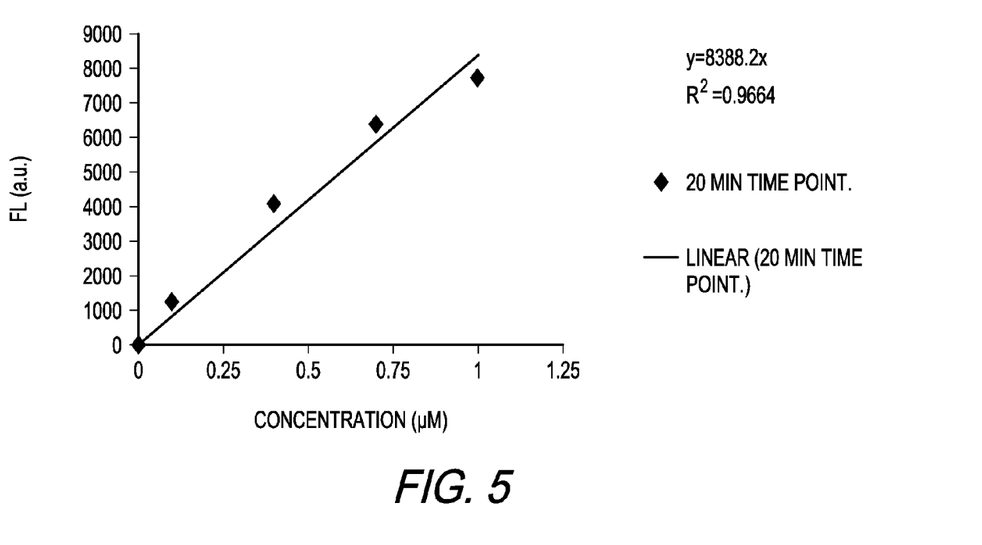
FIG. 5 shows a graph displaying fluorescence as a function of 1-hexanal concentration.

With reference to FIG. 5, the fluorescence response for mPDA as a function of 1-hexanal concentration is displayed, with the background corrected. A linear response is observed form 0.1 to 1 µM 1-hexanal. The data points are the average of triplicate samples. The signal is measured at 20 minutes after the aldehyde is added to the phenylene diamine solution. Under these conditions, 10.8 mM mPDA, 65.5 mM NaCl, 50 mM citrate (pH 2.5), 0.2% SDS at 25° C., a solution limit of detection (LOD) of 0.1 µM can be achieved.

Figure 6:
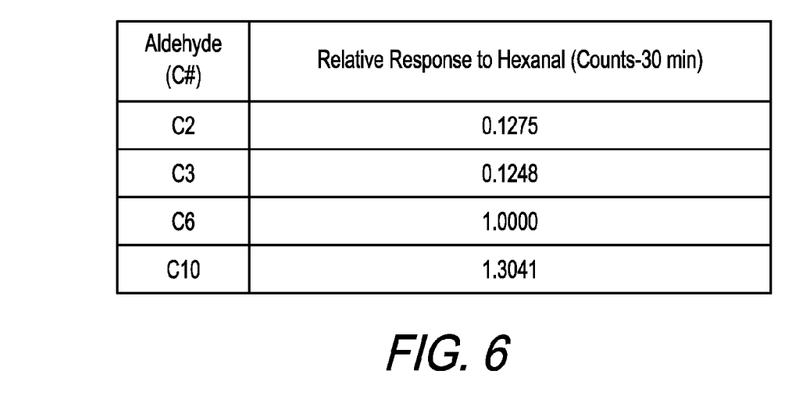
FIG. 6 shows a chart depicting the relative fluorescence as a function of aldehyde chain length.

With reference to the chart in FIG. 6, mPDA exhibits a differential response for aliphatic aldehydes as a function of chain length. The chart reflects the fluorescence signal at 20 minutes after aldehyde addition, and the following conditions: 5.4 mM mPDA, 33 mM NaCl, 50 mM citrate (pH 2.5), 15% EtOH, and 0.1% SDS. The signal is measured at 20 minutes and this time-slice serves as pseudo end-point analysis method. For aliphatic aldehydes the relative response increases with aliphatic chain length. The response of acetylaldehyde is only 12% of the response observed for 1-hexanal. In contrast, the response of decyl ($C_{10}$) aldehyde is 30% greater than for 1-hexanal.

Figure 7:
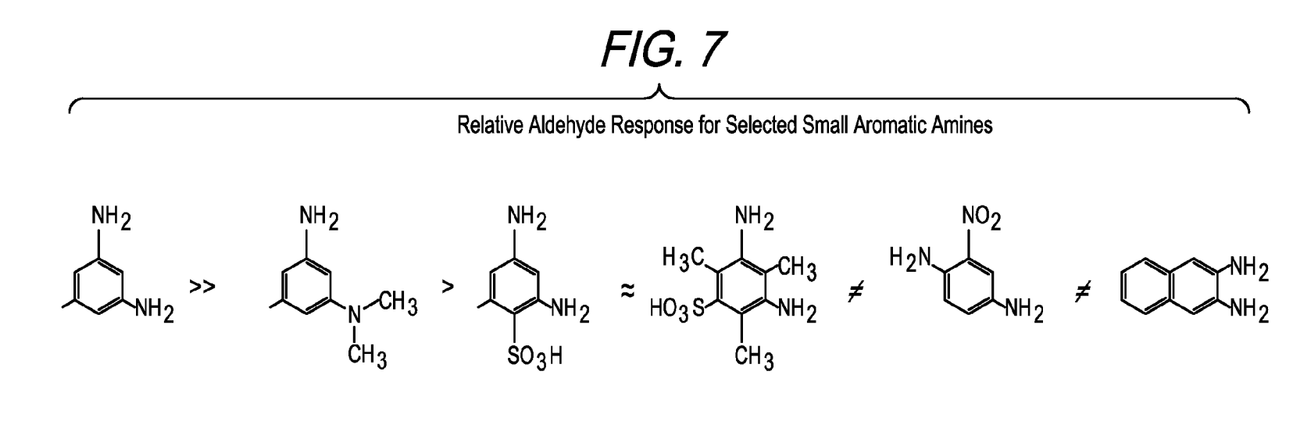
FIG. 7 shows a chart depicting the relative fluorescence of selected small aromatic amines.

The nature of the aromatic diamine is also important to consider in employing the method of the present invention. O-PDA is highly reactive and undergoes rapid general oxidation. The high reactivity of o-PDA precludes its use as an aldehyde sensor in the preferred embodiment of the present invention. With reference to FIG. 7, the relative fluorescence response of a subset of diamines is displayed and illustrates the influence of both position and electronic effects on the aldehyde fluorescence response. Traditional aromatic electron donating and withdrawing effects should modulate the reactivity and susceptibility of the phenylene diamine derivative toward polymerization. An aldehyde response was not observed for both nitrophenylenediamine and naphthalenediamine under the preferred conditions, even when exposed to excess aldehyde. It has been found that aldehyde detection is based on the modulation of the polymerization of the reaction. If the molecule chosen is highly reactive and easily induced to polymerization then general oxidants can stimulate the reaction process and may limit its utility as a sensor. On the other hand, if the molecule is "too" stabilized, the polymerization process becomes inhibited and cannot be adequately stimulated by aldehyde and will require a much stronger oxidant to yield a response.

The present invention also includes a device for employing the method of the present invention. The device comprises a breath chamber preferably made of plastic and having a substrate in the breath chamber. The substrate is made from the materials discussed above and preferably silica. The substrate supports a carbonyl containing moiety from an animal's breath, e.g. aldehydes. The device also includes a fluid chamber. The fluid chamber includes an aqueous solution comprising an alcohol (e.g., 15% EtOH), a salt (e.g., NaCl), a surfactant (e.g., SDS), and a buffer (e.g. citrate). The solution can also comprise a phenylene diamine derivative such as mPDA.

The following example demonstrates one way to use the present invention to determine whether the sample breath of a human contains measurable aldehyde concentration and the concentration of the aldehyde in the breath. Employing the methodology discussed above, a series of fluorescence measurements are preformed to provide standards for various specific aldehydes and mixtures thereof that are known to be contained in a human breath sample (a population), and standards for concentrations of such various standards and mixtures thereof. Using these standards, the presence in a sample of human breath of a particular aldehyde or mixture of aldehydes and the concentration of such particular aldehyde or mixture of aldehydes can be determined. In general in one embodiment, the steps are as follows:

a. Capturing the aldehydes from the human breath sample on silica;
b. Forming a solution comprising a salt, a buffer, a surfactant in an alcohol in mildly acidic conditions;
c. Adding a phenylene diamine derivative to the solution of step b;
d. Eluting the captured aldehydes into the solution of step c;
e. Determining the fluorescence signal of the solution of step c;
f. Determining the fluorescence signal of the solution of step d;
g. Subtract the fluorescence signal from step e from the fluorescence signal from step f; and
h. Comparing the net resulting fluorescence signal from step g with standard fluorescence of known aldehydes (a calibration curve, i.e., a response to known concentrations via an assay) to determine the concentration of aldehydes in the fluorescing solution. Simply put, this is a comparison of "y" axis values to provide the "x" axis value, or alternatively, solve of x knowing y and the calibration function y=f(x).

In another embodiment of the present invention, the substrate can be pre-loaded with an active reactive capture agent which covalently attaches to the CCM (the "Agent") including without limitation a fluorescent hydrazine or aminooxy compound. Some examples of aminooxy compounds are as follows: aminooxy 5(6) tetramethylrhodamine (aminooxy 5(6) TAMRA), with a single isomer of either 5 or 6 preferred; and aminooxy 5(6) carboxyfluorescein (aminooxy 5(6) FAM), with a single isomer of either 5 or 6 preferred, for example aminooxy-C5-5-FAM. Others include aminooxy 7-amino-3-acetyl-4 methylcourmarin-6-sulfonic acid; 5-aminoxy acetic acid rhodamine B; and dinitrophenylhydrazin. In the foregoing examples, the reactive group is specified without the linkage group, which would be well known to those of skill in the art. In addition to the foregoing, the hydrazine or hydrazide versions are included within the present invention. Preferably the Agent is somewhat polar.

For example, for a substrate consisting of 200 mg of 50-270 mesh (300-50 μm) particle with a bed diameter of 12.5 mm, the amount of the Agent can be from 5.5 mg to 0.1 mg, and preferably from 2.5 mg to 0.4 mg.

In yet another embodiment of the present invention, a two-solution methodology is used. After the substrate is loaded with the CCM, the CCM is eluted into a "rinse" solution comprising generally 30% ethanol and preferably 50 mM citrate, 30% ethanol at ph 2.5. The Agent is added to the rinse solution thereby resulting in painted CCM. This solution is then passed through another substrate, preferably a silica frit stack, to capture the painted CCM. The painted CCM is then eluted from the substrate with the painted CCM captured therein using a second "rinse" solution comprising greater than 50% acetonitrile and preferably 90% ethanol. One of the benefits of this second embodiment is that a baseline reading is not necessary to remove noise.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." Additionally, the words "herein, "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while methods are presented in a given order, alternative embodiments may perform the method, in a different order, and some method steps may be deleted, moved, added, subdivided, combined, and/or modified to provide alternative or subcombinations. Further any specific numbers noted herein are only examples: alternative implementations may employ differing values or ranges.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the detected fluorescence corresponds to the concentration of carbonyl containing moieties in the biological sample, and wherein the biological sample is human breath, the carbonyl containing moiety is an aldehyde and the phenylene diamine derivative is m-phenylene diamine.

2. The method of claim 1 wherein the carbonyl containing moiety is selected from the group consisting of aldehydes, ketones, carboxylic acids and mixtures thereof.

3. The method of claim 2, wherein the aldehydes are aliphatic.

4. The method of claim 1, wherein the biological sample is human breath.

5. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the phenylene diamine derivative is selected from the group of meta-phenylene diamine derivatives and mixtures thereof.

6. The method of claim 1, wherein the fluorescence has a measurable emission band at 505 nm.

7. The method of claim 1, wherein the fluorescing solution is maintained at below about 35° C.

8. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the aqueous salt solution comprises an alcohol, a salt, a surfactant and a buffer.

9. The method of claim 8 where the buffer is citrate.

10. The method of claim 8 wherein the alcohol is chosen from the group consisting of R—OH, where R is a straight or branched chain aliphatic group, and mixtures thereof.

11. The method of claim 9, wherein the alcohol is ethanol.

12. The method of claim 8, wherein the salt is NaCl.

13. The method of claim 8, wherein the surfactant is sodium dodecyl sulfate.

14. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein pH of the aqueous solution ranges from 2 to 4.5.

15. The method of claim 8, wherein the molar ratio of the phenylene diamine derivative to the salt ranges from 0.03 to 0.5.

16. The method of claim 1, wherein the carbonyl containing moiety is eluted from silica.

17. The method of claim 1, wherein the carbonyl containing moiety is a C1 to C12 carbonyl containing organic molecule.

18. A method of detecting and measuring the concentration of a carbonyl containing moiety in a biological sample, the method comprising
   a) isolating the carbonyl containing moiety from the biological sample;
   b) adding the carbonyl containing moiety to an aqueous solution containing a phenylene diamine derivative to form a fluorescing solution; and
   c) measuring the fluorescence emitted from the fluorescing solution at a pre-determined wave length.

19. The method of claim 18, wherein the biological sample is a breath sample.

20. The method of claim 18, wherein the concentration of the carbonyl containing moiety in the biological sample is determined using the fluorescence measurement.

21. The method of claim 1, wherein the phenylene diamine derivative comprises pyridinium,4-[2-[4-(diethylaminio)phenyl-ethenyl]-1-[1-(3,5-diminobenzamide)-pentylamino-5-oxyhexyl].

22. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the phenylene diamine derivative comprises any one or mixtures of the following:

where R1, R2, R3, R4 are each independently selected from the group consisting of H, alkyl, substituted alky, alkoxy, substituted alkoxy, acyl, acylamino, acyloxy, amino, substituted amino, aminocarbonyl, aminothiocarbonyl, aminocarbonylamine, aminothiocarbonylamino, aminocarbonyloxy, aminosulfonyl, aminosulfonyloxy, aminosulfonylamino, amidino, carboxyl, carboxyl ester, (carboxylester) amino, (carboxy ester) oxy, cyano, halo, hydroxy, SO3-, sulfonyl, substituted sulfonyl, sulfonyloxy, thioacyl, thioal, alkylthio, substituted alkylthio, acyl, substituted aryl, heteroaryl, substituted heteroaryl, cycloalkyl, substituted cycloalkyl, heterocycles, and substituted heterocycles.

23. A method of detecting carbonyl containing moieties in a biological sample, the method comprising adding a fluorescence chromophore to an aqueous salt solution to thereby form a fluorescence chromophore solution; adding a carbonyl containing moiety from the biological sample to the fluorescence chromophore solution to thereby form a fluorescing solution; and detecting fluorescence from the fluorescing solution.

24. The method of claim 23, wherein the fluorescence chromophore is a phenylene diamine derivative.

25. The method of claim 24, wherein the fluorescence chromophore is m-phenylene diamine.

26. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the phenylene diamine derivative is polymerized by the carbonyl containing moiety in the solution to form a fluorogenic species.

27. A method of detecting carbonyl containing moieties in a biological sample, the method comprising adding a phenylene diamine derivative to an aqueous salt solution to thereby form a phenylene diamine solution; adding a carbonyl containing moiety from the biological sample to the phenylene diamine solution to thereby form a fluorescing solution; and detecting fluorescence from the fluorescing solution, wherein the phenylene diamine derivative is housed in an ampule.

28. The method of claim 18, wherein the fluorescing solution generates a broad optical absorbance band at 405 nm and an associated emission band at 505 nm.

29. The method of claim 18, wherein the aqueous solution contains a surfactant, and the level of fluorescence over time varies with the concentration of the surfactant.

30. A method for detecting carbonyl containing moieties in a biological sample, the method comprising the steps of providing a substrate having an active reactive capture agent incorporated therein, capturing on said substrate carbonyl containing moieties from the biological sample, and forming a solution comprising painted carbonyl containing moieties.

31. The method of claim 26, wherein there is no precipitate in the fluorescing solution which at the time of measurement, substantially interferes with the measurement of the fluorogenic species.

* * * * *